United States Patent [19]

Mayeaux

[11] Patent Number: 4,589,971
[45] Date of Patent: May 20, 1986

[54] MOISTURE ANALYZER

[75] Inventor: Donald P. Mayeaux, Prairieville, La.

[73] Assignee: The Permutit Company, Paramus, N.J.

[21] Appl. No.: 615,049

[22] Filed: May 29, 1984

[51] Int. Cl.[4] ............................................. G01N 27/46
[52] U.S. Cl. ........................................ 204/430; 73/29; 73/336.5; 55/218; 55/337; 55/498; 204/409
[58] Field of Search ............... 204/430, 415, 418, 409, 204/1 W; 73/29, 336.5; 338/34, 35; 55/337, 218, 498, 509

[56] References Cited

U.S. PATENT DOCUMENTS

| | | | |
|---|---|---|---|
| 3,001,918 | 9/1961 | Czuha, Jr. | 204/430 X |
| 3,105,214 | 9/1963 | Blythe et al. | 73/336.5 X |
| 3,188,283 | 6/1965 | Cole | 204/430 X |
| 3,240,693 | 3/1966 | Gardner | 204/430 |
| 3,244,602 | 4/1966 | Glass et al. | 204/430 X |
| 3,823,082 | 7/1974 | Czuha, Jr. | 204/430 |
| 3,886,057 | 5/1975 | Bredeweg | 204/430 |
| 3,926,745 | 12/1975 | Czuha, Jr. | 204/430 X |
| 3,934,454 | 1/1976 | Simo | 73/29 |
| 4,149,403 | 4/1979 | Muldary et al. | 73/29 |
| 4,210,508 | 7/1980 | Bergson | 204/430 |
| 4,221,058 | 9/1980 | Zagorzycki | 73/29 X |

*Primary Examiner*—John F. Niebling
*Assistant Examiner*—Nam X. Nguyen
*Attorney, Agent, or Firm*—Llewellyn A. Proctor

[57] ABSTRACT

An apparatus, viz., a moisture analyzer, for the detection, and measurement of moisture in trace amounts in fluid streams, especially gas streams. The moisture analyzer is characterized as (A) a cell assembly constituted of a compartmented structure (i) a first compartment separated from a second compartment by a partitioning semi-permeable membrane through which moisture can be passed, said first compartment including a fluid, or gas inlet into which a moisture-containing fluid, especially a gas, can be admitted, and a fluid, or gas outlet from which fluid, or gas, can be expelled, (ii) the second compartment containing an electrical circuit which includes at least one pair of electrically isolated electrodes located in close proximity one to another, upon which electrodes can be disposed a hydroscopic substance, or electrolyte, e.g., $P_2O_5$, which is electrically conductive when wet and in contact with both electrodes, (B) a direct current power source of voltage sufficient to electrolyze said hydroscopic substance, or electrolyte, when it is wetted by moisture passed through said semi-permeable membrane from the first compartment to said second compartment, (C) current measuring means connected in circuit with said power source for measuring the water content of said hydroscopic substance, or electrolyte as a function of the current delivered by said power source in electrolyzing said hydroscopic substance.

12 Claims, 11 Drawing Figures

MOISTURE ANALYZER

BACKGROUND OF THE INVENTION

I. Field of the Invention

This invention relates to a moisture (water) analyzer, or apparatus for the detection, and measurement of moisture in fluid streams. In particular, it relates to apparatus for the detection, and continuous accurate measurement of moisture in small and infinitesmal, or trace concentrations in flowing gas streams.

II. Background and Prior Art

Industrial operations often require the detection, and continuous accurate measurement of moisture in process streams, e.g., hydrocarbon streams. In natural gas production, for example, the gas contains many constituents other than gaseous hydrocarbons. Many are undesirable contaminants, e.g., glycols, methanolamine, iron oxide particulates (rouge), and methanol antifreeze which is often injected into natural gas lines. Water is one of the most abundant of the constituents of natural gas, and it is often present as liquid droplets, or in vapor form, or both. Water in condensed form can generally be removed by mechanical means. Water in vapor form, however, is not so easily removed. Consequently, in many operations, it is necessary to continuously and accurately measure the amount of water vapor present in gas; even when the moisture is present only in trace amounts, or concentrations measured in parts per million (ppm), based on the total volume (or weight) of the gas. Pipeline and natural gas distribution companies, e.g., expect relatively dry gas to be delivered into their distribution systems. Wet gas can cause many operating problems; not the least of which is that the gas distributor may be required to pay for water vapor left in the gas stream. It is therefore important to this industry, and to many other industries, that the moisture content of the gas be accurately detected, and measured at the point of delivery to pipeline or gas distribution systems.

Various apparatus and methods are known for the measurement of water in gases. Some utilize electrolytic sensors; some measure dew point by optical means; some utilize a vibrating crystal; some are capacitance and impedance detectors; and some simply use wet chemical measurement techniques. In U.S. Pat. No. 2,830,945 to F. E Keidel there is described an instrument or apparatus, which utilizes an electrolytic sensor for the determination, and measurement of the amount of moisture in gases. The analysis is carried out in a special cell which combines water absorption with electrolysis. An absorbent, electrically conductive when wet, is dispersed as a thin viscous film of hydroscopic electrolyte within a Teflon tube in contact with two platinum electrodes, constituting a portion of an external electrical circuit. Moisture in the gas flowing through the cell is absorbed by the hydroscopic film, a partially hydrated phosphorus pentoxide, the water being electrolyzed to oxygen and hydrogen. The absorbed water is quantitatively electrolyzed at the electrodes by the application of a dc voltage greater than the decomposition potential of the water. The current produced in the external circuit is directly proportional to the water content of the gas and serves as a direct measurement of the water content of the gas.

Whereas the apparatus of Keidel and those of others have been used with varying degrees of success, none are ideal. Some of these instruments are not specific to water such that contaminants interfere with proper operation of the instrument. Some are dependent on the flow rate of the stream being measured, and often the sensor is easily damaged by contaminant liquids and solids. The instrument becomes unresponsive, and recovery slow after the instrument is slugged by water.

OBJECTS

It is, nonetheless, a primary objective of the present invention to obviate these and other deficiencies of prior art instruments used for the analysis of trace moisture in fluid streams, particularly moisture-containing gas streams, e.g., natural gas, ethylene, refrigerants and various chemical and refinery process streams in which the water concentration must be detected, limited, and controlled at relatively low levels.

A particular object is to provide a new and improved apparatus, or instrument, for such usage which utilizes an electrolytic sensor for the detection, and measurement of moisture in such streams.

A further, and more specific object is to provide apparatus as characterized for the specific detection, and measurement of moisture in a flowing gas stream in small and infinitesmal concentrations which is independent of the rate of flow of the gas stream, is stable over long periods of operation, and not upset or readily damaged by liquid or solid contaminants.

THE INVENTION

These objects and others are achieved in accordance with the present invention embodying apparatus which, in combination, includes a cell assembly characterized as a compartmented structure, (i) a first compartment separated from a second compartment by a partitioning semi-permeable barrier, or membrane through which moisture can be passed, said first compartment including a fluid, or gas inlet into which a sampled moisture-containing fluid, especially a gas, can be admitted, and a fluid, or gas outlet through which the sampled fluid, or gas, can be expelled, or discharged, (ii) the second, or adjacent, compartment containing an electrical circuit which includes at least one pair of electrically isolated electrodes located in close proximity one to another, upon which electrodes can be disposed a hydroscopic substance, or electrolyte, which is electrically conductive when wet and in contact with both electrodes, a direct current power source of voltage sufficient to electrolyze said hydroscopic substance, or electrolyte, when wetted by moisture passed through said semi-permeable membrane from said first compartment to said second compartment, and current measuring means connected in circuit with said direct current power source for measuring the water content of said hydroscopic substance as a function of the current delivered by said power source in electrolyzing said hydroscopic substance, or electrolyte.

A key and novel feature of the cell assembly relates to the use of a semi-permeable barrier, or membrane for separation of the first compartment, within and through which the moisture-containing fluid or gas is passed, and the second compartment within which is contained the one or more pairs of electrically isolated electrodes upon which is disposed the hydroscopic substance, or electrolyte. Water molecules, dependent upon their concentration within the sampled fluid passing through the first compartment, are transported through the membrane to the hydrostatic substance, or electrolyte, where the water is disassociated, or electrolytically decomposed to its elemental components, hydrogen and oxygen by action of the electrical current upon the hydroscopic substance, or electrolyte. An electrical signal, is produced which is directly proportional to the number of water molecules which are transported through the membrane, and this signal in turn is directly related to the moisture, or water vapor concentration within the sampled fluid, or gas. Hence, this signal is readily measured and converted electrically to a readout, e.g., as parts of water per million parts of fluid, by volume, i.e., ppm v/v, or in pounds of water, per million cubic feet of fluid, i.e., lbs/mmcf. Unlike previous instruments of this type, the dependency upon sample flow rate is eliminated, and replaced by a far more accurate type of physical measurement. Moreover, the separation of the hydroscopic substance, or electrolyte, from direct contact with the sampled fluid due to the presence of the semi-permeable membrane protects the electrolyte from solids and liquids contamination. It also prevents the electrolyte from being leached, or washed-out by slugs of liquids. For these reasons, inter alia, the detector response remains stable over long periods of time.

The characteristics of a preferred trace moisture gas analyzer, and the principle of its operation, will be more fully understood by reference to the following detailed description, and to the attached drawings to which reference is made in the description. The various features and components in the drawings are referred to by numbers, similar features and components being represented in the different views by similar numbers. Subscripts are used in some instances with numbers where there are duplicate features and components, or to designate a sub-feature or component of a larger assembly.

IN THE DRAWINGS

FIG. 3 depicting the filter in perspective view, FIG. 3A being a view taken through section 3A—3A of FIG. 3, and FIG. 4 depicting the filter in half section;

Figure 1:
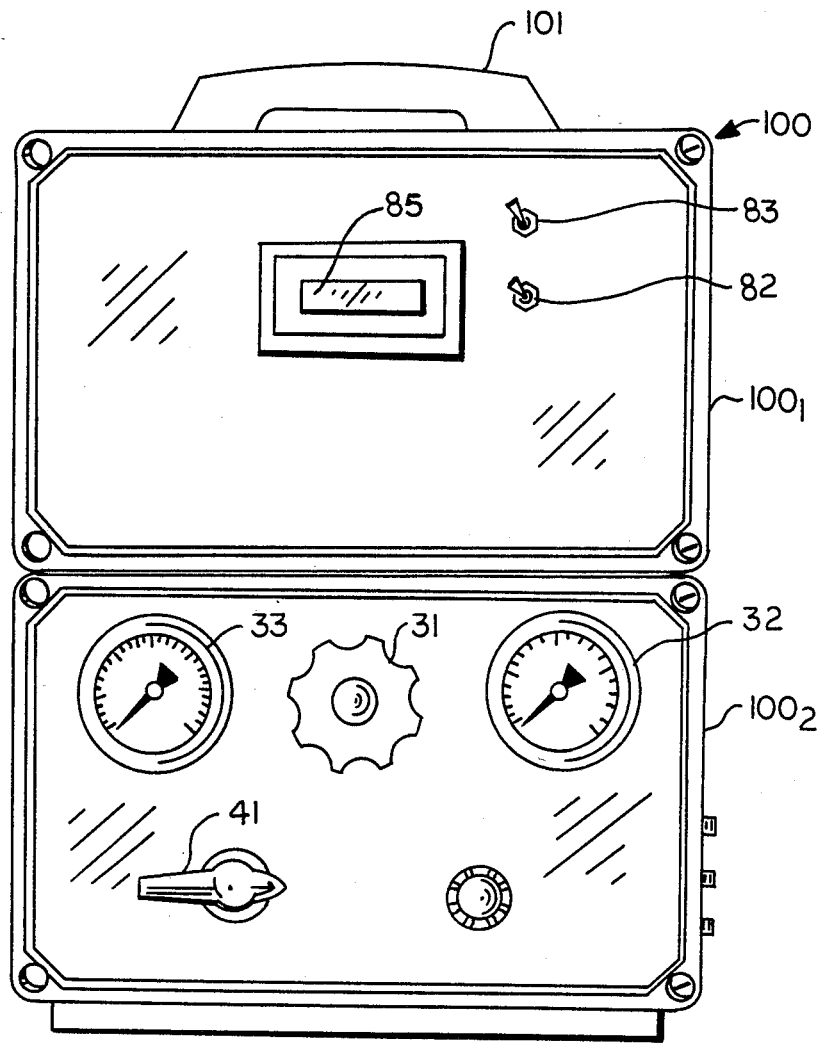
FIG. 1 depicts a front elevation view of the moisture analyzer, this view showing the housing which is constituted of an upper section which houses principally the electrical components, batteries, and readout, and a lower section which houses principally the mechanical components.
Figure 2:
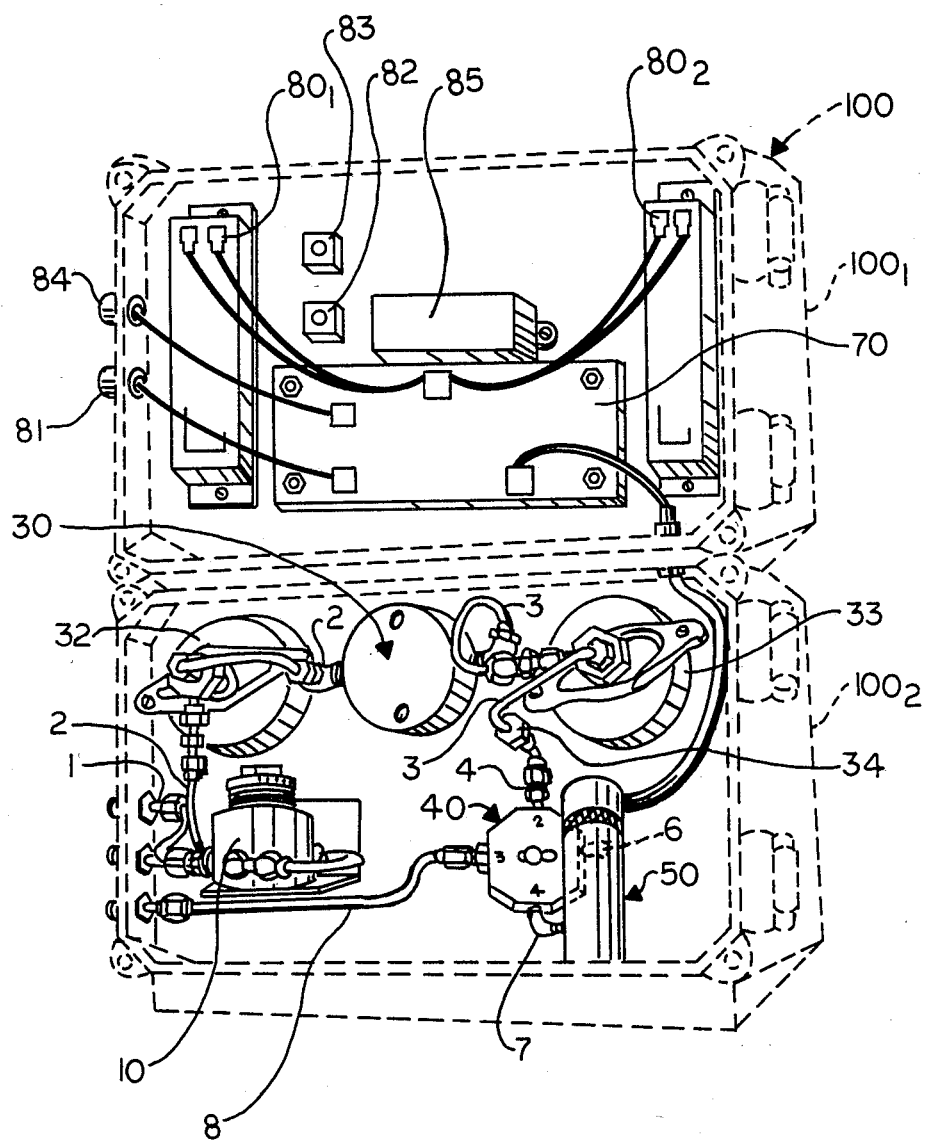
FIG. 2 depicts a rear elevation, isometric view of the moisture analyzer, the housing being outlined in phantom with the objective of showing the principal components contained with the upper and lower sections of the housing, and their relationship one component with another.

Referring to FIGS. 1 and 2 (and FIG. 8), generally, there is shown a two segmented case or housing 100 constituting an upper compartment $100_1$, and lower compartment $100_2$; each compartment $100_1$, $100_2$ including top, bottom, and oppositely disposed side walls as well as a front wall and rearward door (not shown) which is hinged to a side wall and opens outwardly. The case or housing 100, provided with a carrying handle 101, may, e.g., be constructed of aluminum or other metal for rugged field use. Within the lower compartment $100_2$ there is included a filter 10 with low water adsorption characteristics where solids contaminants are removed from an entering sample fluid, a gas, the moisture level of which is to be measured. A pressure regulator 30, adjustable via knob 31 (FIG. 1), is employed to reduce the sample pressure to a level desired, e.g., to approximately 5 to 10 pounds per square inch gauge (psig). Gauges 32, 33 located on opposite sides, i.e., upstream and downstream, of the pressure regulator 30, respectively allow the line sample pressure (gauge 32) and analyzer pressure (gauge 33) to be observed (FIG. 1). A flow restrictor 34 located downstream of the analyzer pressure gauge 33 maintains a constant flow with a given analyzer pressure (gauge 33), and hence the moisture analyzer is not flow sensitive within a wide range of flow rates. This eliminates any need for using problem prone flow controllers and rotometers. A cell assembly 50, which constitutes the heart of the moisture analyzer, is located downstream of a four-way, or selector valve 40. In one position the selector valve 40 allows sample gas to flow through the filter 10 and pressure regulator 30 circuit while by-passing the cell assembly 50 until these apparatus components are in equilibrium with the sampled gas stream. The sample gas stream leaving the instrument can be viewed to determine if serious amount of solids or liquid contaminants are present, thus avoiding unnecessary cell exposure to major amounts of these contaminants. The isolation of the cell assembly 50 in this manner also protects the cell from the high water levels normally present in ambient air. In another position, the moisture-containing sample gas flows into the moisture analyzer and into filter 10, through the regulator 30, flow restrictor 34, selector valve 40 and through the cell assembly 50. The line pressure, or sample pressure is measured by pressure gauge 32 at a point between the filter 10 and pressure regulator 30, and, the analyzer pressure 33 is measured at a point between the flow regulator 30 and flow restrictor 34. The cell assembly 50 can be operated at substantially atmospheric pressure; fluid from the cell assembly 50 after passage therethrough being vented to the atmosphere. The analyzer pressure gauge 33 indicates pressure upstream of the flow control restrictor 34, not the cell assembly pressure.

The upper section of the housing $100_1$ houses the electrical circuitry largely contained upon a circuit board 70, batteries 80, and readout 80. Electrical power is supplied by one of two internal rechargable gell cells, or other type of batteries $80_1$, $80_2$ which can be selected by means of a front panel switch 82. The batteries, in general, are of a type conveniently charged in place and/or the unit operated directly from an automobile cigarette lighter or a 120 vac battery charger/eliminator. The batteries 80, when fully charged as via connection of a charging source to the batteries 80 via the input, or charge jack 81 can be expected to power the unit for several days. The moisture content of a fluid specimen can be read out, e.g., in either ppm v/v or lbs mmcf, by reference to the meter 85, when the instrument is turned on via switch 83. The moisture level can also be recorded, as via plugging a recorder device into jack 84.

Figure 8:
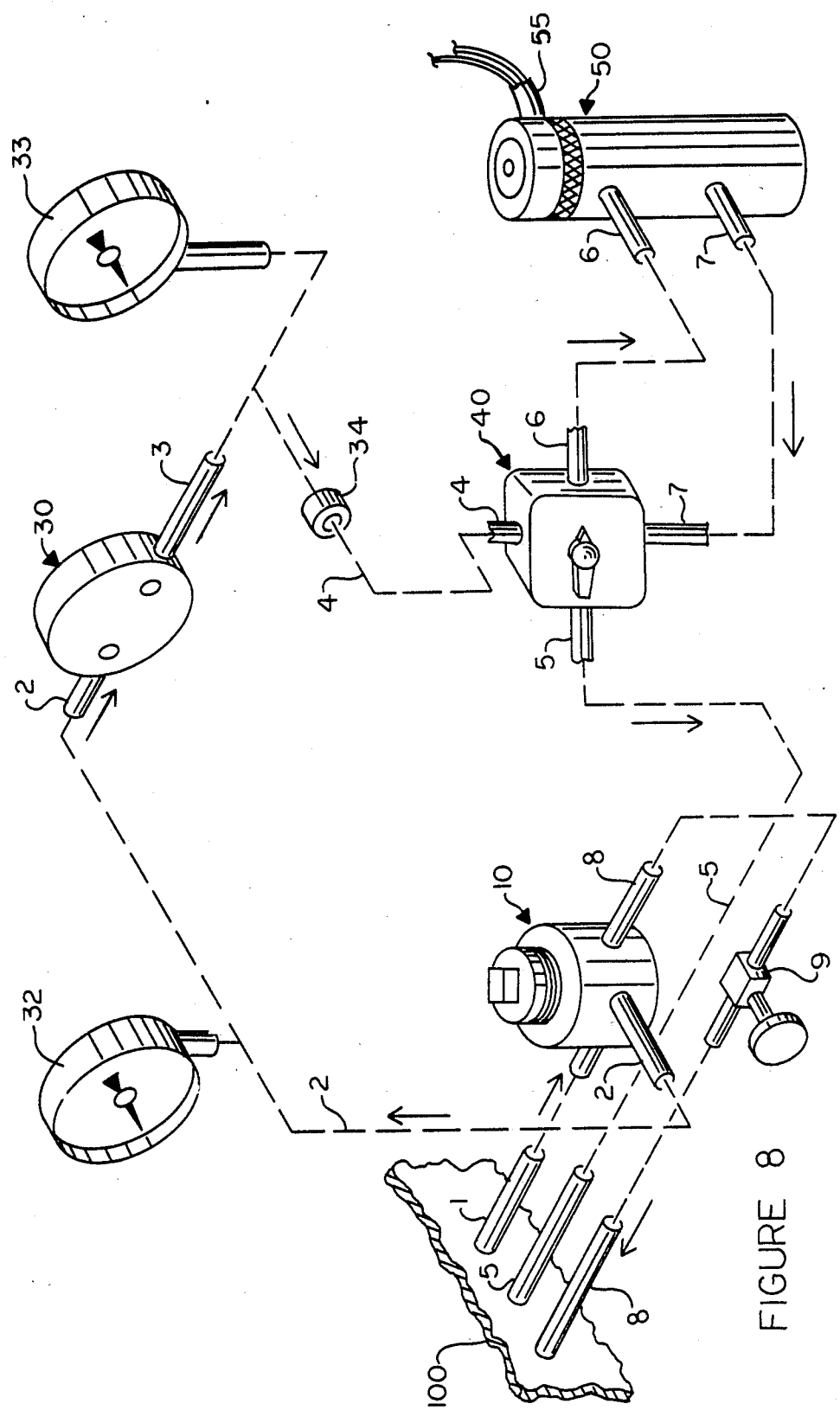
FIG. 8 depicts in exploded fashion, and somewhat schematically, the essential apparatus components of a preferred moisture analyzer.

The flow path of the sample gas in its passage through the analyzer 100 is shown by reference to FIGS. 2 and 8, particularly FIG. 8. A sample gas is introduced into the analyzer 100, the switch 41 (FIG. 1) of the selector valve 40 in a first position, causing the cell 50 to be by-passed. The sample gas, with cell 50 cut out of the circuit, enters the analyzer 100 via line 1, passes into filter 10 and exits therefrom via line 2, passes through the pressure regulator 30 exiting therefrom via line 3 whereupon it passes through the flow restrictor 34 to enter line 4. The gas then passes through the selector valve 40 and exits therefrom via line 5 whereupon it is vented to the exterior. In the alternate switch position (as shown in the figures) the selector valve 40 introduces the cell 50 into the circuit such that sample gas enters the analyzer 100 via line 1, flows through filter 10 to exit therefrom via line 2, enters pressure regulator 30 via line 2 and exits therefrom via line 3, flows through the flow restrictor 34, enters the selector valve 40 via line 4 and exits therefrom via line 6 to flow through cell 50. The sample gas passes out of cell 50 via line 7 and then through selector valve 40 to line 5 whereupon it is vented to the exterior. Aerosol and liquid are discharged from filter 10, as subsequently discussed, via line 8 when the by-pass valve 9 is in open position.

Figure 4:
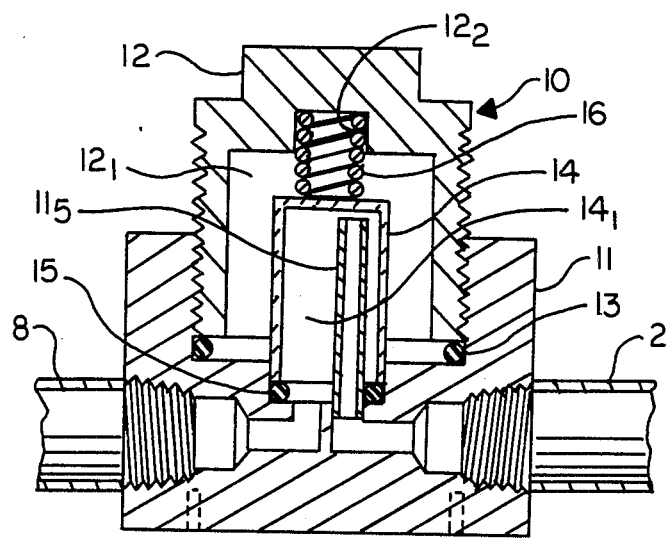
FIGS. 3, 3A and 4 depict the details of a preferred filter, for the separation of solids or other contaminants from the gas specimen entering the moisture analyzer.
Figure 3A:
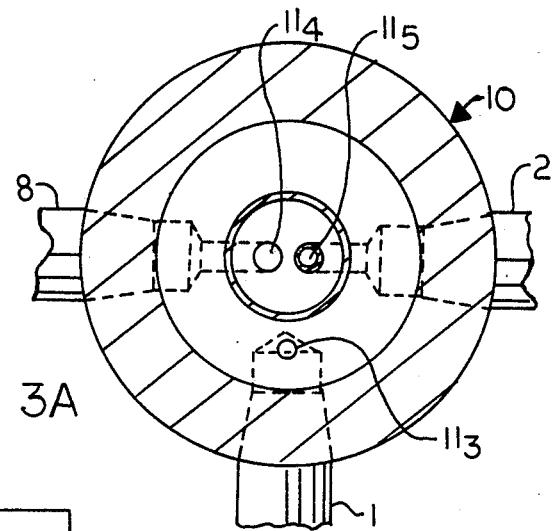
Figure 3:
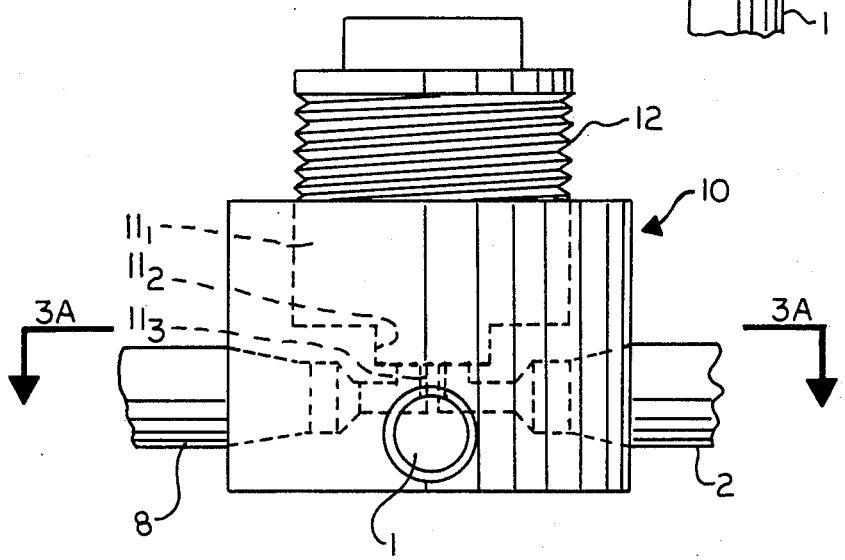

A gas specimen, the moisture level of which is to be measured is, as suggested, first introduced into the filter or filter assembly 10, the details of which are described by reference to FIGS. 3, 3A and 4. This type of filter removes aerosols and fine solids from the sample gas, particularly liquids which may be entrained in the gas. The filter assembly 10 is constituted of a large diameter outer filter body 11 provided with an internally threaded central opening $11_1$, a bottom well $11_2$, an inlet port $11_3$, and outlet ports $11_4$, $11_5$. Connections are provided for line 1 for communication with inlet port $11_3$; for line 8 for communication with outlet port $11_4$; and for line 2 for communication with outlet port $11_5$. An externally threaded plug 12, provided with an open center $12_1$, is threadably engaged with said threaded central opening $11_1$, of the outer body 11; and when tightened down against an o-ring 13, provides a sealed enclosure. A bottom opened, porous wall filter thimble 14 is contained within the sealed enclosure. The open bottom end of the filter thimble 14 is seated within the well $11_2$, and rests atop an o-ring 15, the thimble being retained in place via the tensioned helical spring 16 one end of which rests atop the filter thimble 14 and the other of which is retained within the well $12_2$ within the externally threaded plug 12. Two chambers are thus provided: one an outer chamber $12_1$ formed by the internal wall of the plug 12 and the external wall of the filter thimble 14, and the other $14_1$ within the filter thimble 14. The outer chamber $12_1$ is connected via port $11_3$ with line 1; line 1 being connected with a sample gas source (not shown). The chamber $14_1$ inside the filter thimble 14 is connected via outlet port $11_4$ with line 8, a vent line leading to the analyzer exterior. The inside chamber $14_1$ is also connected via outlet port $11_5$ which takes the form of a riser enclosed within the filter thimble 14, the upper end of which terminates near the inside top surface of the filter thimble 14, and the bottom end of which is directly communicated with line 2 which connects with the pressure regulator 30.

In the operation of the filter, sample gas is introduced via line 1, and inlet port $11_3$ into outer chamber $12_1$ (FIG. 3A), gas passing through the porous wall of filter thimble 14 to enter into chamber $14_1$ inside the thimble. Solid particulates are retained on the exterior porous wall of the filter thimble 14, and any aerosols which may be present are caused to coalesce. Contaminating liquids exit via the port $11_4$ and are vented, or discharged to the exterior via line 8. The remainder of the moisture-containing sample gas rises within the inside of the thimble 14 for transport through the riser tube $11_5$ and discharge through line 2.

A feature of the filter assembly 10 is that it can be readily assembled, and disassembled as for cleaning, or repair. The filter assembly 10 is readily disassembled, as for cleaning, by unscrewing and removing the plug 12 from the outer body 11. This done, the helical spring 16, thimble 14 and o-rings 13, 15 are readily removed; and readily reassembled after completion of the cleaning.

The riser tube $11_5$ of the filter assembly 10, it will be observed, is designed so that the sample gas flow to the cell assembly 50 will not contain any contaminating solids, or liquids. The sample gas inlet $11_3$, liquid and sample gas outlets $11_4$, $11_5$, respectively, it will be observed are all located within the outer filter body 11. No sample gas connection, or lines of any kind, are located on the filter plug 12, this enabling the filter to be serviced without having to disconnect, and connect, sample gas lines; with consequent elimination of sources of leakage, and complexities.

The cell, or cell assembly 50, referring now to FIGS. 5, 6, 7 and 7A, is constituted of a cylindrical shaped inner member having an enlarged rearward portion and a smaller diameter forward portion, the forward smaller diameter portion of which is notched and carries exposed, separated wire electrodes. This member is referred to as a cell bobbin 51, the principle function of which is to provide a support for the pair of separated wire electrodes 52, the hydroscopic electrolyte 53 which is spread upon the exposed section of the electrodes 52, semi-permeable membrane 54, and electrical cable 55 which connects with the wire electrodes 52. The cell bobbin assembly also includes an open centered upper bobbin cap 56, the function of which is to retain the semi-permeable membrane 54 in place and seal it against the small diameter portion of the cell bobbin 51 so that sample gas cannot directly contact the electrolyte 53. Sample gas introduced through the open center $56_1$ of the upper bobbin cap 56 thus directly contacts the membrane 54, but cannot directly contact the electrolyte 53. A lower bobbin 57 also covers a portion of the wire electrodes 52 and electrolyte 53, and provides an additional seal to protect against sample gas intrusion into the electrolyte 53. The two wires forming the electrodes 52 are separated one from the other, each separately wound about the small diameter end of the cell bobbin 51, and each wire lies within separated external grooves (FIGS. 7, 7A) which maintains this separation. The terminal ends of each of the two wire electrodes are projected through small lateral openings $51_{1A}$ ($51_{1B}$; 180° apart from $51_{1A}$ on opposite sides of the cell bobbin, not shown) to an axial opening running through the center of the small diameter end of the cell bobbin 51. The separation of the wire pair is maintained by a central pin 58 which fixes the separated ends of the wires in place against the wall of the axial opening. The opposite terminal ends of the pair of wire electrodes 52 is attached via soldered ends $52_1$, $52_2$ to the two wire ends $55_1$, $55_2$ of the pair of wires forming the cable 55. The cable 55, which is attached to the wire electrodes 52 traverses through the interior of the cell bobbin 51 and is projected through a lateral opening 59 within the enlarged rearward end of said cell bobbin 51.

In assembly, after the cable 55 is mounted within the cell bobbin 51, and its terminal ends projected through the lateral side opening 59, of the cell bobbin 51, epoxy resin can be poured through the large axially located opening 60, prior to insertion of the cap 61, the resin entering into the opening 59, to set, harden, and seal in the cable 55 and provide cable strain relief. Some of the resin also enters the oppositely disposed shallow opening 62, and sets and hardens therein to aid in securing the cable in fixed position. The back cap 61 can then be set in place. When epoxy resin is thus poured into the opening 60, and the back, or end opening sealed by the bobbin back plug 61, the center hole $61_1$ allows excess epoxy to escape. Excess resin is wiped away. The resin inside the cell bobbin assembly 51 then sets, and hardens. The entire small diameter forward portion of the cell bobbin, with its component parts assembled, is snugly fitted within the tubular shaped cell body 63 provided with a slot opening $63_1$ for alignment with the opening $56_1$ within the upper bobbin cap 56. This sub-assembly forms a unitary and major sub-assembly of the cell 50. This sub-assembly, when fitted into the cell housing 65 essentially completes the cell 50.

The cell housing 65 is characterized as a tubular shaped member, with an enclosed forward end. The cell housing 65 is provided with a sample gas inlet $65_1$ and gas outlet $65_2$. The large open end of the cell housing 65 is internally threaded, i.e., provided with threads $65_3$, for threadable engagement with the external threads $63_2$ of cell body 63. The cell bobbin cell assembly, inclusive of cell body 63, in fully assembled form is threadably engaged with the cell housing 65 and sealed via an o-ring 64. In assembly, the sample gas inlet $65_1$ provides a means for the ingress of the sample gas into the cell assembly 50, and the sample gas outlet $65_2$ provides a means for the egress of sample gas from the cell assembly 50.

Figures 5, 6, 7, 7A:
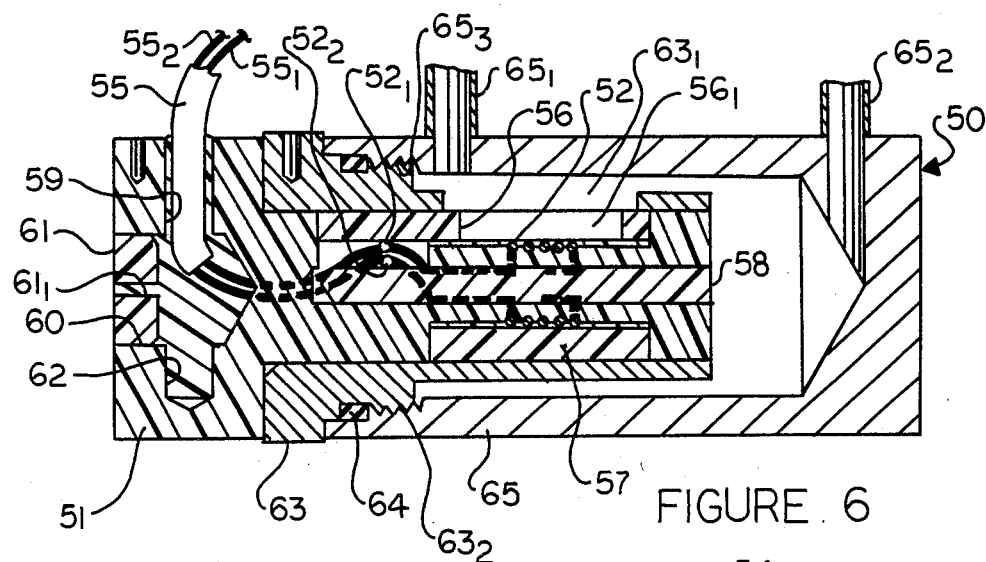
FIG. 5 depicts a preferred cell assembly.
FIG. 6 depicts a full section view of the cell assembly.
FIG. 7 depicts a fragmentary view of a portion of the pair of electrodes, and its relationship to the semi-permeable membrane shown in section.
FIG. 7A depicts an enlarged further fragmented view showing the relationship between the electrodes, semi-permeable membrane, and electrolyte.

The cell bobbin 51, as stated, provides a means for holding the pair of electrode wires 52, electrolyte 53, and membrane 54 in their correct relationships. Electrolyte 53 can be poured or smeared atop the exposed pair of wire electrodes 52, the semi-permeable membrane 54 wrapped around the electrodes 52 to cover them, the bobbin caps 56, 57 put in place and the cell bobbin 51, so-assembled, then the forward portion thereof snugly pressed into the cell body 63; and the cell unit assembled. As also stated, the cell bobbin 51 also provides a housing for attachment of the electrical cable 55 to the electrode wires 52, and strain relief for the cable 55. In its preferred form the electrodes 52 are constituted of a pair of durable highly electrically conductive wires, most preferably a pair of platinum wires, wound around the small diameter projecting forward portion of the cell bobbin 51 each located within separately shaped grooves cut into the external surface wall of the cell bobbin 51 for carrying these members (FIGS. 7, 7A). For example, the grooves within which the parallel pair of thread thin electrode wires 52 are located can be cut approximately 0.004 inches deep; each of the two grooves carrying a wire totalling 48 threads/inch for a total of 96 threads/inch; and consequently adjacent wire thread loops are 0.010 inch apart at any point. The cell, in its essence, is constructed in a manner that permits the electrolytically sensitive components of the cell to be readily removed from its housing for inspection, cleaning or replacement if this should ever be necessary. The cell is easily manufactured and assembled.

The semi-permeable membrane 54 isolates the electrolytic portion of the cell from the sampled gas, and hence protects the electrolyte 53 from solids and liquids contamination. Slugs of liquid thus cannot wash out the electrolyte 53, and hence stable, long trouble-free periods of operation are assured. There can be no migration of the electrolyte 53 to other parts of the cell. The use of the membrane 54 eliminates any requirement for precise sample fluid flow control. The transport rate of water molecules from the sample gas stream via the membrane 54 into the electrolyte 54 is primarily controlled by water concentration and membrane characteristics. Various materials are suitable for use as membranes. A preferred membrane material, e.g., is unsintered polytetrafluoroethylene (Teflon) because this material is almost totally immune from chemical attack by sample fluid components. Its characteristics remain stable and water flow through the membrane 54, and into the electrolyte 53, is entirely dependent upon the concentration of water in the sampled gas. In this regard, only a small portion of the water molecules actually contained in the sample gas streams are actually transported through the membrane 54 into the electrolyte 53. It is only necessary that the amount of water molecules that are transported through the membrane 54 be directly related to the number of water molecules that are contained in the sampled gas stream. As a consequence of this, cell response is independent of the rate of sample gas flow after a small threshold flow level has been exceeded. Exemplary of other materials from which membranes can be formed are such polymeric materials as polymethylmethacrylate, polyethylene, polypropylene, polyurethane, epoxy resins, polyesters, polyglycols, polyoxyalkylene diols, phenolic resins, melamine resins, and the like. A preferred electrolyte is phosphorous pentoxide ($P_2O_5$).

The operation of the trace gas moisture analyzer is best illustrated by reference to FIG. 8. In this figure, the essential components of the moisture analyzer are shown in exploded, and in somewhat schematic form. In initiating the analysis of a moisture-containing gas stream, or stream which may contain moisture, the several components of the instrument, with the exception of the cell 50, are first purged with the gas stream. The position of the selector valve 40, via use of selector switch 41 (FIG. 1), is first set so that the cell assembly is isolated from the flow of sample gas. Sample gas thus flows into the instrument via line 1 into the filter 10, out of filter 10 via line 2 through the pressure regulator 30, out of pressure regulator 30 via line 3 through the flow restrictor 34, then via line 4 through selector valve 40, and the gas is then vented to the atmosphere via line 5. Liquids from the filter 10, if any, are vented via line 8 to the atmosphere. Gauge 32 records the pressure line sample pressure, and gauge 33 the analyzer pressure. The selector valve 40, after the cell components are in equilibrium with the gas stream, is then repositioned via the selector switch 41 (FIG. 1) to connect the cell assembly 50 in circuit with other cell components. In this position of the selector valve 40, as shown in FIG. 8 (and FIGS. 1 and 2), cell assembly 50 now receives gas from line 4, and selector valve 40 via line 6, gas leaving the cell assembly 50 via line 7, to again pass through the selector valve 40 whereupon it is then vented to the atmosphere via line 5. Thus, in calibrating the instrument, and in conducting the analysis of a sample gas, the sample gas enters the instrument via line 1, passes through the filter 10, passes via line 2 to pressure regulator 30, leaves pressure regulator 30 via line 3, and after passage through the restrictor 34 passes via line 4 into the selector valve 40. The sample gas stream enters the cell assembly 40 via line 6, exits the cell assembly 50 via line 7, again passes through the regulator valve 40, and line 5 from which it is vented to the atmosphere.

Figure 9:
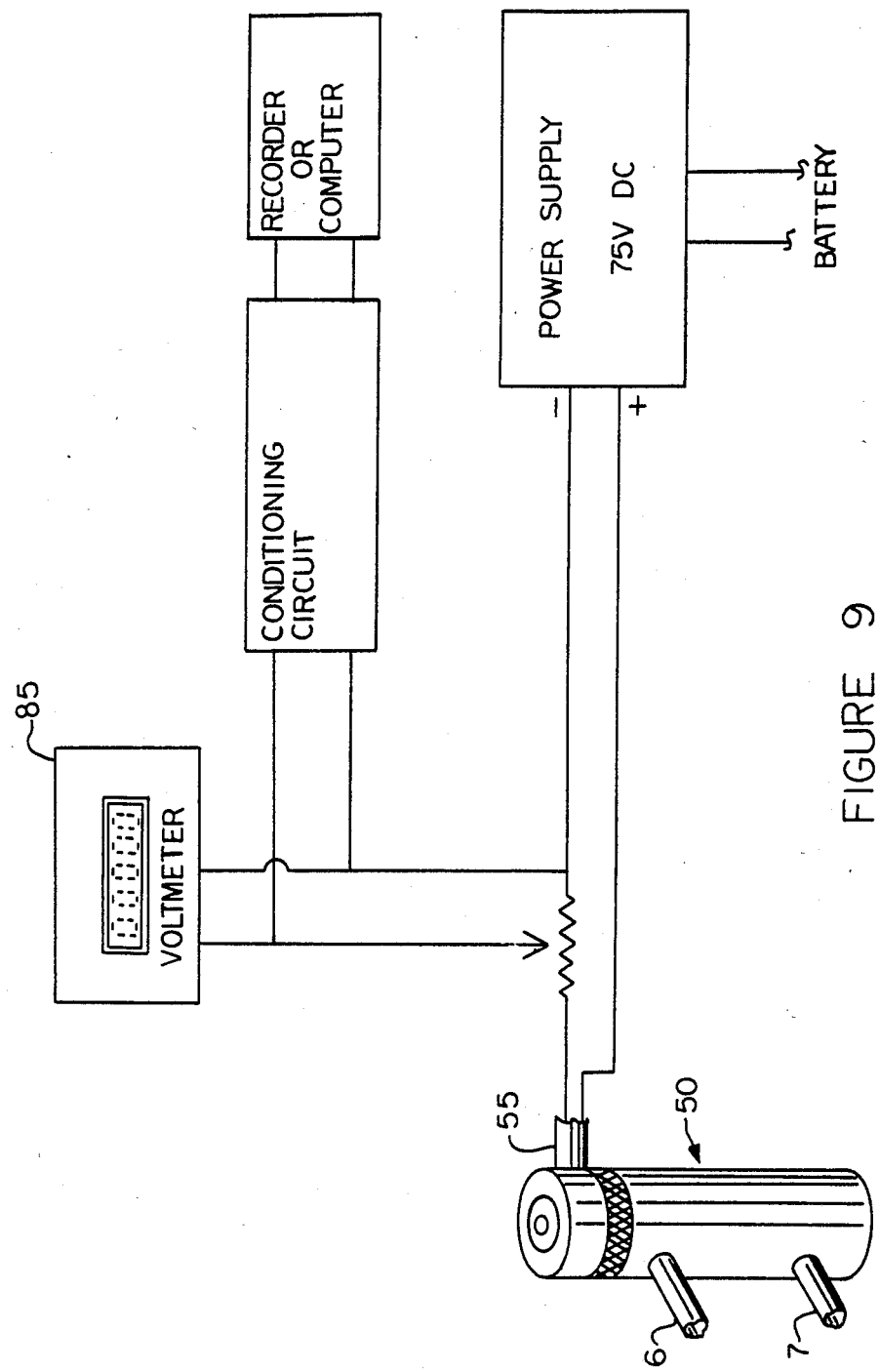
FIG. 9 depicts schematically an electrical wiring diagram of preferred circuitry, readout, and recording components.

A preferred type of electrical circuit associated with the cell assembly 50 is depicted schematically by reference to FIG. 9. In its more simple form, a voltmeter can be used for measuring and displaying the moisture concentration in the sample gas directly in terms of unit quantity of water per unit quantity of sample gas, this eliminating any necessity for range switching. It also provides a precise means for direct readout of the moisture concentration. Battery power is adequate for such purpose, but where required the power can be stepped up, e.g., from 6 V or 12 V to 75 V direct current. The voltmeter reads the potential difference that represent the current flow from the cell, this value being representative of the moisture contained within the sample gas. The output from the cell can also be recorded, or sent to a computer, the raw signal from the cell being first sent through a conditioning circuit which buffers the signal, and regulates it in accordance with some desired scale.

It is apparent that various modifications and changes can be made without departing the spirit and scope of the invention.

Having described the invention, what is claimed is:

1. In combination, an apparatus for detecting and measuring the amount of moisture in a moisture-containing gaseous stream which utilizes a cell assembly characterized as a compartmented structure, a first compartment separated from a second compartment by a partitioning semi-permeable membrane through which moisture can be passed, which comprises an open-end cell housing forming said first compartment, said housing including an enclosing wall, a gas inlet within said wall into which a sampled moisture-containing gas can be admitted, and a gas outlet within said wall through which the sampled gas can be discharged, a cell bobbin assembly providing said second compartment, said cell bobbin assembly including a forward portion which is projected into the open-end of said cell housing, enclosed and detachably mounted therein, the cell bobbin carrying an electrical circuit, the external face of the forward portion of said cell bobbin assembly being provided with continuous circumferential grooves of helical orientation which wind about the central axis of said cell bobbin assembly and carry at least one pair of exposed thread-like wire electrodes which constitute a portion of said electrical circuit, and upon which can be disposed a hydroscopic electrolyte which is electrically conductive when wet and in contact with both wires of an electrode pair, the semi-permeable membrane which separates said first and second compartments one from the other being carried upon said forward face of the cell bobbin to cover said exposed wire electrodes, and said hydroscopic electrolyte, such that when a moisture-containing gas is admitted via the gas inlet and discharged via the gas outlet of said first compartment and contacted with an exposed side of the semi-permeable membrane within said first compartment moisture can be transported from said moisture-containing gas for contact with said hydroscopic electrolyte within said second compartment, a direct current power source of voltage sufficient to electrolyze said hydroscopic electrolyte when wetted by moisture passed through said semi-permeable membrane from said first compartment to said second compartment, current measuring means connected in circuit with said direct current power source for measuring the water content of said hydroscopic electrolyte as a function of the current delivered by said power source in electrolyzing said hydroscopic electrolyte, a filter, a pressure regulator connected in series with said filter, a four-way selector valve connected in series with said filter, said pressure regulator and to the gas inlet and gas outlet of said cell assembly, whereupon the moisture-containing sample gas can be passed through the circuit containing the filter and pressure regulator while by-passing the cell assembly, and alternately the moisture-containing sample gas can be passed serially through the circuit containing filter, pressure regulator and cell assembly.

2. The apparatus of claim 1 wherein the filter is constitute of an assembly which includes, in combination, an outer hollow body provided with a central opening and a plug which can be threadably engaged thereupon for enclosing and sealing said central opening to form an outer chamber, the outer hollow body including a fluid inlet into the bottom of said central opening, and an outlet port and a riser outlet over which a bottom opened filter thimble is mounted to form an inner chamber, such that a solids and liquids contaminated moisture-containing fluid sample can be admitted via said fluid inlet at the bottom thereof into the outer chamber formed by the central opening of the hollow body and enclosing plug, the sample gas passed through the filter thimble into the inner chamber to filter out solids, and separate out liquid contaminants from the moisture-containing fluid sample, the liquid contaminates discharged via the outlet port within said inner chamber, and the remaining portion of said moisture-containing fluid sample passed through the riser outlet.

3. The apparatus of claim 2 wherein the outer hollow body is a bottom enclosed tubular member, the central opening of which is internally threaded, the plug is an externally threaded body for threadable engagement with the central opening of said outer hollow body and provided with a central opening, and the bottom opened filter thimble is mounted within a well and held in place by a tensioned spring seated within the top of said plug which rests against the bottom enclosure of said thimble.

4. The apparatus claim 1 wherein the partitioning semi-permeable membrane which separates said first and second compartments of the cell assembly is a polymeric substance.

5. The apparatus of claim 4 wherein the polymeric substance is unsintered polytetrafluoroethylene.

6. The apparatus of claim 1 wherein the cell bobbin assembly includes a generally cylindrical shaped inner member having an enlarged diameter rearward portion and a smaller diameter forward portion, the smaller diameter portion of the cell bobbin is notched and carries the exposed wire electrodes which are covered by said semi-permeable membrane.

7. The apparatus of claim 6 wherein the electrodes carried within said grooves of the cell bobbin assembly are thread-like, and the terminal ends of the electrodes are passed through the interior of the cell bobbin assembly and electrically connected to an electrical cable which is projected outwardly through the enlarge diameter rearward portion of the cell bobbin assembly.

8. The apparatus of claim 7 wherein the electrical cable is in electrical contact with a dc power supply source to provide voltage for electrolysis of said hydroscopic electrolyte, and current measuring means by virtue of which the moisture content of the sampled gas can be read.

9. The apparatus of claim 8 wherein the current measuring means includes a digital readout.

10. In combination, an apparatus for detecting and measuring the amount of moisture contained in a moisture-containing gaseous stream which utilizes a cell assembly characterized as a compartmented structure, a first compartment separated from a second compartment by a partitioning semi-permeable membrane through which moisture can be passed, which comprises a cell assembly which includes a tubular cell housing forming said first comparment, said housing having an enclosing wall, an open-end and a closed end, a gas inlet within said wall into which a sampled moisture-containing gas can be admitted, and a gas outlet within said wall through which the sampled gas can be discharged, a cell bobbin assembly providing said second compartment, said cell bobbin assembly including a forward cylindrical shaped end which is projected into the open-end of said tubular housing, and enclosed and detachably mounted therein, the cell bobbin carrying an electrical circuit, the external face of the forward cyclindrical shaped end of said cell bobbin assembly being provided with continuous circumferential grooves which wind circumferentially around said cylindrical shaped end of said cell bobbin and carry a pair of exposed thread-like wire electrodes which constitute a portion of said electrical circuit, and upon which can be disposed a hydroscopic electrolyte which is electrically conductive when wet and in contact with both wires of the electrode pair, the semi-permeable membrane which separates said first and second compartments one from the other being carried upon the grooved face of the cylindrical shaped end of the cell bobbin to cover said exposed wire electrodes, and hydroscopic electrolyte, such that when a moisture-containing gas is admitted via the gas inlet and discharged via the gas outlet of said first compartment formed by said housing, moisture can be transported from said moisture-containing gas for contact with said hydroscopic electrolyte within said second compartment, a direct current power source of voltage connected through an electrical cable extending through the interior of the cell bobbin assembly and electrically connected to the terminal ends of the electrodes of said cell bobbin assembly sufficient to electrolyze said hydroscopic electrolyte when wetted by moisture passed through said semi-permeable membrane from said first compartment to said second compartment, current measuring means connected in circuit with said direct current power source for measuring the water content of said hydroscopic electrolyte as a function of the current delivered by said power source in electrolyzing said hydroscopic electrolyte, a filter, a pressure regulator connected in series with said filter, a four-way selected valve connected in series with said filter, said pressure regulator and to the gas inlet and gas outlet of said cell assembly, whereupon the moisture-containing sampled gas can be passed through the circuit containing the filter and pressure regulator while by-passing the cell assembly, and alternatively the moisture-containing sampled gas can be passed serially through the circuit containing the filter, pressure regulator and cell assembly.

11. The apparatus of claim 10 wherein the filter is constituted of an assembly which includes, in combination, an outer hollow body provided with a central opening forming a wall the inside face of which is internally threaded, a plug the interior of which is provided with a central opening forming a wall the outer face of which is externally threaded such that the plug can be threadably engaged to said outer hollow body for enclosing and sealing said central opening to form an outer chamber, the outer hollow body including a gas inlet into the bottom of said central opening, and an outlet port and a riser outlet over which a bottom opened filter thimple is mounted to form an inner chamber, such that solids and liquids contaminated moisture-containing gas sample can be admitted via said gas inlet at the bottom thereof into the outer chamber formed by the central opening of the hollow body and enclosing plug, the sample gas passed through the filter thimble into the inner chamber to filter out solids, and separate out liquid contaminants from the moisture-containing gas sample, the liquid contaminates discharged via the outlet port within said inner chamber, and the remaining portion of said moisture-containing gas sample passed through the riser outlet.

12. The apparatus of claim 11 wherein the outer hollow body is a bottom enclosed tubular member, and the bottom opened filter thimble is mounted within a well and held in place by a tensioned spring seated within the top of said plug which rests against the bottom enclosure of said thimble.

* * * * *